(12) United States Patent
Tuli et al.

(10) Patent No.: US 7,459,545 B2
(45) Date of Patent: Dec. 2, 2008

(54) CHEMICALLY SYNTHESIZED ARTIFICIAL PROMOTER FOR HIGH LEVEL EXPRESSION OF TRANSGENES AND A METHOD FOR ITS SYNTHESIS

(75) Inventors: Rakesh Tuli, Lucknow (IN); Samir V. Sawant, Lucknow (IN); Pradhyumna K. Singh, Lucknow (IN); Shiv K. Gupta, Lucknow (IN)

(73) Assignee: Council Of Scientific & Industrial Research, New Delhi (IN)

( * ) Notice: Subject to any disclaimer, the term of this patent is extended or adjusted under 35 U.S.C. 154(b) by 266 days.

(21) Appl. No.: 10/661,478

(22) Filed: Sep. 15, 2003

(65) Prior Publication Data

US 2005/0267299 A1 Dec. 1, 2005

Related U.S. Application Data

(62) Division of application No. 09/263,692, filed on Mar. 5, 1999, now Pat. No. 6,639,065.

(30) Foreign Application Priority Data

Nov. 9, 1998 (IN) .............................. 3322/DEL/98

(51) Int. Cl.
 C07H 21/04 (2006.01)
 C12Q 1/68 (2006.01)
 C12N 15/63 (2006.01)

(52) U.S. Cl. ......................................... 536/24.1; 435/6
(58) Field of Classification Search ....................... None
 See application file for complete search history.

(56) References Cited

OTHER PUBLICATIONS

Vankan et al, *The EMBO Journal*, 8(12):3875-3882 (1989).

*Primary Examiner*—David Guzo
*Assistant Examiner*—Michele K. Joike
(74) *Attorney, Agent, or Firm*—Sughrue Mion, PLLC

(57) ABSTRACT

The invention relates to a chemically synthesized artificial promoter comprising a DNA sequence designed for the target level and pattern of gene expression, by strategically putting together several signature sequences identified by sequence alignment and statistical analysis of a large database constructed for this purpose.

7 Claims, 3 Drawing Sheets

DESIGNING OF OVERLAPPING OLIGOS FOR SYNTHESIS OF
ARTIFICIAL PROMOTER

```
  1 GTCGACCATCATTTGAAAGGGCCTCGGTAATACCATTGTGGAAAAAGTTG
    CAGCTGGTAGTAAACTTTCCCGGAGCCATTATGGTAACACCTTTTTCAAC

51 GTAATACGGAAAAAGAAGATTCATCATCCAGAAAAGGTGTGGAAAAGTTG
    CATTATGCCTTTTTCTTCTAAGTAGTAGGTCTTTTCCACACCTTTTCAAC

101 TGGATTGCGTGGAAAAAGTTCGATCTGACCATCTCTAGATCGTGGAAAAA
    ACCTAACGCACCTTTTTCAAGCTAGACTGGTAGAGATCTAGCACCTTTTT

151 GTTCACGTAAGCGCTTACGTACATATGTGGATTGTGGAAAAAGAAGACGG
    CAAGTGCATTCGCGAATGCATGTATACACCTAACACCTTTTTCTTCTGCC

201 AGGCATCGGTGGAAAAAGAAGCTTGTACGCTGTACGCTGACGATAGATAG
    TCCGTAGCCACCTTTTTCTTCGAACATGCGACATGCGACTGCTATCTATC

251 ATACACGTGCACGCGTCCACTTGACGCACAATTGACGCACAATGACGCCA
    TATGTGCACGTGCGCAGGTGAACTGCGTGTTAACTGCGTGTTACTGCGGT

301 CTTGACGCTACTTCACTATATATAGGAAGTTCATTTCATTTGGATTGGAC
    GAACTGCGATGAAGTGATATATATCCTTCAAGTAAAGTAAACCTAACCTG

351 ACGTGTTGTCATTTCTCAACAATTACCAACAACAACAAACAACAAACAAC
    TGCACAACAGTAAAGAGTTGTTAATGGTTGTTGTTGTTTGTTGTTTGTTG

401 ATTATACAATTACTATTTACAATTACATCTAGAT
    TAATATGTTAATGATAAATGTTAATGTAGATCTA
```

FIG.1 DESIGNING OF OVERLAPPING OLIGOS FOR SYNTHESIS OF
ARTIFICIAL PROMOTER

```
  1 GTCGACCATCATTTGAAAGGGCCTCGGTAATACCATTGTGGAAAAAGTTG
    CAGCTGGTAGTAAACTTTCCCGGAGCCATTATGGTAACACCTTTTTCAAC

51 GTAATACGGAAAAAGAAGATTCATCATCCAGAAAAGGTGTGGAAAAGTTG
    CATTATGCCTTTTTCTTCTAAGTAGTAGGTCTTTTCCACACCTTTTCAAC

101 TGGATTGCGTGGAAAAAGTTCGATCTGACCATCTCTAGATCGTGGAAAAA
    ACCTAACGCACCTTTTTCAAGCTAGACTGGTAGAGATCTAGCACCTTTTT

151 GTTCACGTAAGCGCTTACGTACATATGTGGATTGTGGAAAAAGAAGACGG
    CAAGTGCATTCGCGAATGCATGTATACACCTAACACCTTTTTCTTCTGCC

201 AGGCATCGGTGGAAAAAGAAGCTTGTACGCTGTACGCTGACGATAGATAG
    TCCGTAGCCACCTTTTTCTTCGAACATGCGACATGCGACTGCTATCTATC

251 ATACACGTGCACGCGTCCACTTGACGCACAATTGACGCACAATGACGCCA
    TATGTGCACGTGCGCAGGTGAACTGCGTGTTAACTGCGTGTTACTGCGGT

301 CTTGACGCTACTTCACTATATATAGGAAGTTCATTTCATTTGGATTGGAC
    GAACTGCGATGAAGTGATATATATCCTTCAAGTAAAGTAAACCTAACCTG

351 ACGTGTTGTCATTTCTCAACAATTACCAACAACAACAAACAACAAACAAC
    TGCACAACAGTAAAGAGTTGTTAATGGTTGTTGTTGTTTGTTGTTTGTTG

401 ATTATACAATTACTATTTACAATTACATCTAGAT
    TAATATGTTAATGATAAATGTTAATGTAGATCTA
```

FIG.2 RESTRICTION ENZYME SITES IN ARTIFICIAL SYNTHETIC PROMOTER

```
SA                                                              T
ac                                                              f
lc                                                              i
II                                                              I
GTCGACCATCATTTGAAAGGGCCTCGGTAATACCATTGTGGAAAAAGTTGGTAATACGGAAAAAGAAGAT
                 25                          50

X                 X
                                        m                 b
                                        n                 a
                                        I                 I
TCATCATCCAGAAAAGGTGTGGAAAAGTTGTGGATTGCGTGGAAAAAGTTCGATCTGACCATCTCTAGAT
      75                  100                       125

X                   S    N
         m                   n    d
         n                   a    e
         I                   B    I
         |                   I    |
CGTGGAAAAAGTTCACGTAAGCGCTTACGTACATATGTGGATTGTGGAAAAAGAAGACGGAGGCATCGGT
         150                      175                     200

H                               M              M
             i                               l              f
             n                               u              e
             d                               I              I
             3                               |              |
GGAAAAGAAGCTTGTACGCTGTACGCTGACGATAGATAGATACACGTGCACGCGTCCACTTGACGCACA
             225                      250                   275

ATTGACGCACAATGACGCCACTTGACGCTACTTCACTATATATAGGAAGTTCATTTCATTTGGATTGGAC
                 300                      325                       350

ACGTGTTGTCATTTCTCAACAATTACCAACAACAACAAACAACAAACAACATTATACAATTACTATTTAC
                      375                      400

X
         b
         a
         I
AATTACATCTAGAT
   425
```

FIG: 3    PRIMER FOR INTRODUCTION OF ATG CONTEXT IN ARTIFICIAL SYNTHETIC PROMOTER

SEQ ID NO.17
5'AATTACATCTAGATAAACAATGGCTTCCTCCGTAGAAACCCCAACCCGTGAAATCAAA 3'

CHEMICALLY SYNTHESIZED ARTIFICIAL PROMOTER FOR HIGH LEVEL EXPRESSION OF TRANSGENES AND A METHOD FOR ITS SYNTHESIS

CROSS-REFERENCE TO RELATED APPLICATIONS

This Application is a Divisional of U.S. application Ser. No. 09/263,692, filed Mar. 5, 1999, now U.S. Pat. No. 6,639,065 the disclosure of which is incorporated herein by reference.

FIELD OF INVENTION

The present invention relates to a chemically synthesised and theoretically designed promoter for high level expression of transgenes in different organisms and a method for designing of the said promoter. The invention further relates to testing of the said promoter to demonstrate high level activity as compared to the natural Cauliflower Mosaic Virus (CaMV) 35S promoter.

The invention emphasises the development of an artificial DNA sequence on the basis of computational analysis of various genes which express at high level in plants. The invention provides a new outlook in the field of developing artificial transcriptional regulatory elements that act in cis on genes. The present invention takes pride in claiming that DNA elements that function as efficient regulatory sequences in the cells of higher organisms can be designed and synthesised to achieve desired level of expression on the basis of knowledge deduced from computational biology and bioinformatics.

BACKGROUND OF INVENTION

One of the main objectives of plant genetic engineering is to develop transgenic plants with new characteristics and traits, which may include insect resistance, virus resistance, herbicide resistance, yield enhancement, stress tolerance, nutritional improvement, expression of industrially valuable proteins in economically profitable expression systems, like plants, etc. Many factors contribute to high level expression of genes which code for such desired characteristics, where 'expression' includes transcription, translation and post translational events. The abundance of any one transcript in a cell directly relates to transcriptional events, which in turn depends upon the strength of the promoter from which it is expressed. Thus, for the development of transgenic plants where high level of transgene expression is to be obtained, it becomes absolutely indispensable that the transgene be expressed from a strong promoter, the transcript is stable, it is translated efficiently and that the resultant protein is also stable in plant cell. Each of these steps synergistically contributes to enhancing the level of expression of the product of the transgene.

A promoter can be defined as a pool of cis-acting elements, which work in co-ordination with trans acting transcriptional factors to achieve expression of the gene attached to it. A promoter provides an efficient docking site for RNA polymerase and the related accessory proteins, which in turn contribute to the transcription of the gene situated operably therewith. Thus, as mentioned, promoters are highly specialised DNA sequences which govern the time and efficiency of transcription. A promoter is classified as a constitutive promoter when it is operable almost equally at all times in a given organism, for example, the CaMV 35S promoter. Other promoters are tissue specific or inducible. The strength of a promoter varies depending on the frequency of initiation of transcriptional events. Depending on strength, promoters can further be classified as strong or weak.

Different types of promoters are required in plant biotechnology, depending upon the target use. Constitutive high level expression promoters are most useful to develop transgenic plants for high level production of commercially required proteins. Such high level expression is also desirable in several situations for modifying metabolic pathways and for improving plants to withstand a variety of stress situations.

Previous reports mainly deal with the identification of natural promoter elements in genes and their improvement. These include, the identification of the CaMV 35S promoter by Odell et al., Nature 313: 810-812 (1985), who had shown the strength and constitutive nature of CaMV 35S promoter. Later, Jensen et al. Nature 321: 669-674 (1986), Jefferson et al., EMBO J., 6: 390-3907 (1987), and Sander et al., Nucleic Acids Research, 4: 1543-1558 (1987), showed measurable levels of reporter gene mRNA expressed from 35S CaMV promoter in extracts prepared from leaves, stems, roots and flowers of transgenic plants. The CaMV 35S promoter has been widely used by scientists in the field of plant genetic engineering. Morelli et al., Nature (1985) 315:200-204 described that the CaMV 35S promoter is transcribed at a relatively high rate as evidenced by a ten-fold increase in transcription products as compared to the NOS promoter. Abel et al., Science (1986) 232:738-743, Bevan et al., EMBO J. (1985) 4: 1921-1926, Morelli et al., Nature (1985) 315:200-204, and Shah et al., Science (1986) 233:478-481 described that the 35S CaMV promoter is moderately strong and constitutively active. Therefore, the CaMV 35S promoter has been used to express a number of foreign genes in transgenic plants. Odell et al., Nature 313: 810-812 (1985), described that initiation of transcription from the 35S promoter is dependent on proximal sequences, which included a TATA element, while the rate of transcription was determined by sequences that were dispersed over 300 bp of upstream DNA. Simpson et al., Nature 323:551-554 (1986) described this region as an enhancer region (sequences which activate transcription are termed enhancers).

Subsequently, other workers tried to improve the CaMV promoter. Kay et al, Science 236: 1299-1302 (1987) duplicated a large region (253 bp) of the naturally existing CaMV 35S promoter and reported enhancement in its activity. Odell, et al., Plant Mol. Biol. 10:263-272 (1988), reported the use of a part of the CaMV 35S promoter as an enhancer in the nopaline synthase promoter. Mitsuhara, et al., Plant Cell Physiol. 37 (1): 49-59 (1996) compared many combinations of different CaMV 35S promoter sequence elements. By increasing the number of repeats of the native enhancer element, they obtained enhanced expression of the reporter gene. Ni, et al., The Plant Journal 7(4):661-676 (1995) combined portions of the naturally occurring octopine and mannopine synthase promoters to develop an efficient chimeric promoter. Ellis, et al., EMBO 6:11-16 (1987), reported the use of a natural octopine synthase promoter fragment to enhance the activity of the maize (adh-1) gene.

Other developments include identification of other natural promoter elements for expression of genes in plants. These include the use of the Figwort Mosaic Virus promoter for achieving enhanced expression per U.S. Pat. No. 5,378,619, Rubisco promoter as per U.S. Pat. No. 4,962,028, chimeric CaMV enhanced mannopine synthase promoter as per U.S. Pat. No. 5,106,739, enhanced CaMV 35S promoter as per U.S. Pat. No. 5,322,938, and the glutamine synthetase promoter for organ specific expression in plants as per U.S. Pat. No. 5,391,725.

As of now, attempts have been made to identify the naturally existing promoter sequences to be used as such or to exchange or rearrange parts of natural promoters so as to achieve a higher level of expression. However, in no case an attempt has been made to design an artificial promoter based on knowledge gained from computational analysis of various DNA sequences present upstream of the gene sequence, reported in the database.

SUMMARY OF THE INVENTION

Some of the objectives of this invention are to design a synthetic promoter aimed at achieving the desired level of expression of the target genes in plant cells, but also in bacteria, yeast, lower euckaryotic cells and animal cells, to use such a promoter in combination with specific regulatory elements, to modify it appropriately so as to make it tissue specific, development stage specific, organ specific and or inducible by specific external environmental/applied factors, as well as, providing, a new approach for studying the complexity of the interaction between cis-acting elements and trans-acting factors.

The present invention relates to analysing the gene sequence database for designing promoters for achieving the desired level of expression of transgenes in different organisms and a method for synthesis of the designed promoter. The invention further relates to testing and demonstrating high level of activity of the synthetic promoter as compared to the natural CaMV 35S promoter.

As an example, the invention demonstrates the designing of an artificial DNA sequence on the basis of computational analysis of various genes which express at high level in plants. The invention provides a new look in the field of synthesizing designer/custom made transcriptional regulatory elements. The approach includes the identification of DNA sequences representing, minimal promoter (SEQ ID NO 2, 3 and 5), conserved domain I and its sub domains a, b and c (SEQ ID NO 6), transcription start site context (SEQ ID NO. 4), conserved domain II and its sub domains a, b, c and d (SEQ ID NO 7, 8, 9 and 10), conserved domain III (SEQ ID. NO 11), domain between TATA and TS (SEQ ID NO 12), 5' untranslated leader (SEQ ID NO 13), translational initiation codon contexts (SEQ ID NO 14 and 15) that act cis on the gene and N-terminal amino acids (SEQ ID NO 16) that may give stability to proteins. An example of such a construct designed in this study is SEQ ID NO: 1. The present invention takes pride in claiming that DNA elements that function as efficient promoter regulatory sequences in a variety of tissues and in a wide spectrum of organisms can be designed on the basis of knowledge generated from computational biology and bioinformatics and synthesised. This invention shows that a biological active and efficiently functional promoter can be synthesised to express in even the most complex organisms.

BRIEF DESCRIPTION OF THE ACCOMPNYING FIGURES

FIG. 1 Describes designing of overlapping oligos for synthesis of a double stranded DNA containing a promoter representing (SEQ ID NO. 1).

FIG. 2. Describes restriction sites in the synthetic promoter designed in this study (SEQ ID. NO. 1).

FIG. 3. Shows primer for introduction of ATG context in synthetic promoter, (SEQ ID NOs. 17).

DETAILED DESCRIPTION OF THE INVENTION

As an example, the invention provides a chemically synthesised promoter comprising a DNA sequence for high level expression of trans enes in different organisms, as exemplified by SEQ ID NO 1 and a method for the synthesis of the said promoter.

The invention further provides a method for testing high-level gene expression in plants.

In an embodiment of the invention, a chemically synthesized promoter can comprise a minimal domain (a) as depicted in SEQ ID NO. 2 (for high level expression of genes, i.e., strong promoter) or SEQ ID NO:3 (for low level expression of genes, i.e., weak promoter) and their derivatives comprising variations as seen in Tables 1 and 2 respectively, functioning as TATA contexts in reference to artificial promoter falling between the positions −26 to −43 (The numbering of nucleotides is such that +1 indicates the first nucleotide of the transcription start site).

In another embodiment of the invention, the chemically synthesised promoter further comprises SEQ ID No. 4 and its derivatives comprising of variations as seen in Table 3 functioning as consensus sequences for a transcription start site in a artificial synthetic promoter falling between the positions −6 to +1.

In yet another embodiment of the invention, the chemically synthesised promoter further comprises minimal domain (b) as depicted in SEQ ID No. 5 falling between positions −39 to −84 of a synthetic promoter.

In another embodiment of the invention, the chemically synthesised promoter further comprises conserved domain I and its sub domains a, b and c as depicted in SEQ ID No.6 falling between the positions −85 to −130.

In yet another embodiment of the invention, the chemically synthesised artificial promoter further comprises conserved domain II and its sub domains a, b, c and d as depicted in SEQ ID Nos. 7, 8, 9 and 10 falling between the positions −134 to −350.

In yet another embodiment of the invention, the chemically synthesised artificial promoter further comprises conserved domain III as depicted in SEQ ID NO. 11 falling between the positions −209 to −230.

In another embodiment of the invention, the chemically synthesised promoter further comprises SEQ ID NO. 12 functioning as typical sequences between the TATA sequence and transcription start site falling between the positions +1 to −26.

In yet another embodiment of the invention, the chemically synthesised artificial promoter further comprises SEQ ID No. 13 functioning as a 5' untranslated leader, and its translational enhancer 'CAA' type region falling between the positions +1 to +89.

In another embodiment of the invention, the chemically synthesized artificial promoter further comprises SEQ ID NO:14 (for high level expression of genes, i.e., strong promoter) and SEQ ID NO:15 (for low level expression of genes, i.e., weak promoter) and their derivatives comprising variations as seen in Tables 4 and 5 respectively, functioning as consensus sequences around the ATG start codon falling between the positions +83 to +102.

In yet another embodiment of the invention, the chemically synthesised artificial promoter further comprising SEQ ID NO. 16 and its derivatives falling between the positions AA1 to AA4 comprising of variation to the extent as seen in Table 6 where the said amino acids, as indicated at the first four positions, are required at the N-terminus for high level expression of a transgene in cells (AA1-AA4 indicates amino acid one through four of the protein).

In another embodiment, the invention further provides a method for chemically synthesising; a promoter for expressing genes at a high level in different organisms comprising:
a) Classifying genes database into highly and lowly expressed genes based on their signature sequences around certain transcription/translation regulatory points that determine expression of the target genes.
b) Identifying conserved domains of the highly expressed genes as identified in step (a) in critical elements comprising a minimal promoter, conserved domain I and its sub domains a, b and c, conserved domain II and its sub domains a, b, c and d, conserved domain III, region between transcription start and TATA site, 5' untranslated leader, translational initiation codon ATG contexts and N-terminal amino acids.
c) Designing synthetic promoters by placing identified critical sequence elements as given in step (b) above in a coordinated manner as depicted, for example, in SEQ ID. NO 1 or its other combinations to achieve desired level of expression of a reporter or target gene.
d) Carrying out synthesis of the promoter DNA as obtained in step (c) above by synthesising overlapping oligos, as exemplified as the promoter of SEQ ID NO. 1, assembling the said oligos into double stranded DNA as depicted in FIG. 1 and cloning of the said promoter with a reporter gene, or a targeted gene selected for expression.

In yet another embodiment, organisms for high level expression of targeted genes are selected from plants or different parts of plants, including leaves, stems, roots and storage tissues like potato tuber, also in different phyla including dicot plants belonging to widely different families and bacteria.

In yet another embodiment, a method for transient expression of the targeted gene from the said promoter in a variety of different tissues and cells as well as stable expression in different parts of transgenic organisms is achieved.

In yet another embodiment, the mode of expression may be constitutive with preferential expression in certain tissues, like roots in this case, in transient or in stable transgenic organisms from the said artificial promoter.

Another embodiment of the invention provides a method for testing the high level expression from the chemically synthesised promoter, following transient transformation of plant cells by polyethylene glycol (PEG) mediated transformation of plant protoplasts, as well as by biolistic mediated transformation of a variety of tissues followed by the reporter gene assay as compared to the expression from a natural CaMV 35S promoter. For the purpose of the present invention, enhanced expression meant several fold higher activity than that from natural CaMV 35S promoter.

In another embodiment of invention, the activity level of the promoter will depend on the host plan: species or the type of explant used for the said purpose.

In yet another embodiment, the test plants used as reference plants are whole tobacco plant, excised tobacco leaf, isolated tobacco leaf cells, cabbage stem and potato tuber. However, expression was also established in the bacterium Agrobacterium tumefaciens.

Computational analysis was carried out using the software from PC-Gene and database release 18-0 from Oxford Molecular Biology Group, Switzerland. A plant database comprising entries from plant genes only was created from the database CDEM 46 IN. It had 13,393 nucleic acid sequences. Depending on resemblance to a putative motif in the TATA and ATG regions, identified by comparing homology among 36 known highly expressed genes in plants, the database was classified into 262 transcriptionally highly expressed genes. Conserved motifs around the TATA region (Tables 1 and 2), transcriptional start site (Table 3) and translation initiation codon ATG (Tables 4 and 5) were identified for highly (Tables 1, 3 and 4) and lowly (Tables 2 and 5) expressed genes. The databases were then screened for possible conserved domains in the promoter region and further upstream of the coding region (reading frame) of genes. The highly conserved motif sequences along with the relatively less conserved regions and their variations to the extent seen in the Tables 1 and 5 gave characteristic component sequences that were assembled to develop an artificial promoter. The most highly conserved individual sequence motifs were identified as SEQ ID NO:2 to SEQ ID NO:16, and assembled to obtain the promoter regulatory sequence SEQ ID NO:1.

As seen from SEQ ID No. 1, several characteristic domains and the extent of variation can be identified in different regions of promoters by statistical analysis of genes sequence data, as presented in Tables 1 to 5. These domains were viz:
i) Minimal promoter region a) Minimal domain (a): TATA box, as seen in data compiled in Tables 1 (for highly expressed) and 2 (for lowly expressed) genes b) Minimal domain (b)
ii) Domain I (sub domains a, b and c)
iii) Domain II (sub domains a, b, c and d)
iv) Region between minimal promoter and transcription initiation start site
v) Domain III
vi) 5' Untranslated leader region
vii) Translation initiation codon context, as seen in data compiled in Tables 3 (for highly expressed) and 4 (for lowly expressed) genes.
viii) N terminal amino acids, as seen in data compiled in Table 5.

Though the above mentioned different regions are predicted to contribute synergistically in determining the high level activity of a promoter, but not all of them are essential for a lower level of activity of the promoter. Although this invention demonstrates that the individual motifs can be put together to assemble a functionally efficient promoter regulatory region, the variations in the occurrence of individual nucleotides at any given position as seen in Tables 1 to 5, make it obvious that various combinations excluding some of these elements can be functional to different extents.

A minimal promoter in eukaryotes is the DNA sequence proximal to the transcription initiation site. It usually contains an initiator cis element typically located ~30 nucleotides upstream of the transcription start site (Aso, et al., J. Biol. Chem. 269: 26575-26583, 1994). The minimal promoter mainly consists of a sequence commonly called the TATA element. Modulation of the formation or stability of the initiation complex by transacting proteins that bind to distal cis elements requires an intact TATA box (Horikoshi, et al., Cell 54: 665-669, 1998). Zhu. et al. (The plant cell 7: 1681-1689, 1988) showed TATATTTAA as a functional TATA box for the phenylalanine ammonialyase (PAL) promoter. In vitro studies conducted by Mukumoto, et al. (Plant Mol. Biol. 23: 995-1003) showed TATATATA as the sequence required for the plant TATA box. Till date, it is not known if TATATATA can be used as the minimal promoter in plants for expression of transgenes. Moreover, the minimal domain (a) used in this study and as depicted in SEQ ID No. 2 is different from those described in the earlier studies. All promoters in the database, as summarised in Table I have sequence motifs representing SEQ ID NO:2 or its variants within statistically insignificant limits. Table I represents the characteristic feature of TATA in highly expressed genes and the variation in the TATA region as noticed in different genes. The sequence domain as shown in SEQ ID No. 2 is (T/C)T(T/A)(T/C)NTCACTATATATAG N indicates any one of the four nucleotides A, T, G or C can appear at that site) and is referred to as minimal domain (a) with respect to artificial synthetic promoter in this study. Our analysis of the database shows that the position of the sequence identified by us can vary from 40 to 28 nt upstream of the transcription start site. The lowly expressing genes show the TATA consensus as $T_3N_4T_2$TATANNNAT (SEQ ID NO:3) which differs significantly from that found in consensus SEQ ID NO:2, and identified by us as a characteristic sequence in highly expressed genes. Thus the selection of sequence of TATA consensus region and its distance from the transcription start site may determine the level of gene expression. Mukumoto, et al., Plant Mol. Biol. 23: 995-1003 (1993) and Keith and Chua EMBO J.; 5: 2419-2425 (1986) deduced the role of the TATA element by experimental evaluation. Their results established the requirement of a sequence with certain critical nucleotide positions within the TATA element. Mutations at different positions were reported to reduce the activity of promoter considerably. An optimized TATA consensus sequence should be situated at a certain distance from the transcription initiation site for efficient initiation of transcription. A less than proper distance of the TATA element from transcription start site and a widely different variant TATA box sequence can be reduce expression as shown by Zhu, et al., The Plant cell, 7:1681-1689 (1995). Efficient recognition of the TATA element by TBP and TAF (TBP associating factors) regulatory factors determines the efficiency of transcription by RNA polymerase II. Our results identify a distinct sequence that can be employed to express genes in plants.

Another distinct domain in a minimal promoter is minimal domain (b) as depicted in SEQ ID No. 5 and its position in the synthetic promoter is marked in SEQ ID No. 1. We identified a variety of conserved sequences like CCAAT, CCACT, CACAAT, CAACCT, CCCAAT in minimal domain (b). These can be represented as C(C/A) (C/A) (A/C)T to reflect the observed variation. These sequences are more likely present between positions −39 to −84 (i.e. upstream of the transcription initiation site taken as +1), but may be present further upstream, as far as −150 as seen by the database analysis. These sequences were noticed in the database to be typically intervened by the presence of a TGACG box. CCAAT and CCACT have been previously identified, in the case of CaMV virus 35S promoter by Odell, et al., Nature. 313: 810-812 (1985) and in certain other plant promoters and are referred as CAT box. However, minimal domain (b) as identified by us is invariably different from that shown in earlier studies. The utilisation of these sequences in the context of constructing a synthetic promoter is an unique idea in the process of promoter designing, as used by us and claimed here. Further, determining their specific positions and the variation thereof in promoters by comparing different plant genes is also a unique approach in developing a synthetic promoter. We notice the following sequence and variants as minimal domain (b).

```
5' CCACTTGACG CACAATTGAC GCACAAT     (SEQ ID NO: 5)
GAC GCCACTTGAC GCTACT 3'
``` which may act as part of the minimal promoter, both in the sense as well as the antisense direction. Functional activity of the sequence constructed by us by employing a mix of C(C/A) (C/A) (A/C) T and TGACG either in prokaryotes or in eukaryotes and especially in plant cells is a novel part of this invention.

The conserved domain I is as given below:

It is further classified into domains (a), (b) & (c). The accessory domain was determined as conserved between nucleotides (nt) −85 to −130 but was also present upstream up to −200 nt in some of the plant genes. Accessory domain designed by us has repeat elements of certain sequences. This may provide multiple binding sites for the trans-acting transcriptional factors. This may leads to the formation of stable transcriptional complex and hence efficient transcription. In many promoters it is known that certain elements are present in multiple numbers, as in the case of EGFR promoter in mammalian cells, which has multiple GC box as shown by Johnson, et al., J. Biol. Chem 263: 5693-5699 (1988). Also in the case of CaMV 35S promoter, Benfy, P. N and Chua, N-H., Science 250: 959-966 (1990) reported the presence of multiple CAT box and GATA type of elements.

Domain I(a) somewhat resembles, but is different from the GC box reported by Menkens, et al., TIBS 20: 506-510 (1995) and may play a role in the kinetics of opening of the transcription bubble and keeping the minimal promoter in a most active form to enhance transcription reinitiation from the transcription complex at the minimal promoter as suggested by Yean and Gralla, Nucl. Acids Res. 24(14): 2723-2729 (1996). The functional element designed by us is duplicated and is different from any of the earlier reported sequences and was predicted theoretically on the basis of computational analysis, as a possible efficient domain.

5' CACGTGCACGCGT 3' (SEQ ID NO:18)

The number of copies that could contribute to enhancing expression could vary, though three copies were taken by us as an example to demonstrate the principle.

Domain I (b) is also designed to be a trimer of the GATA type cis-acting element, as set forth in SEQ ID NO:19.

5' GATAGATAGATA 3' (SEQ ID NO:19)

The GATA elements are known to associate with the CaMV 35S promoter as shown by Odell, et al., Nature, 313: 810-812 (1985). On the basis of computational analysis, we predict this as a sequence that can be used in combination with other sequences to achieve a high level of transcription. The number of copies has been taken as three as an example, to demonstrate the principle and may be variable.

Domain I (c) is yet another artificial dimeric combination of the GTACGC type of element, as set forth in SEQ ID NO:20, noticed by us as commonly present in the region of −126 to −114 but less commonly present in the region of −90 to −120 nt.

5' GCTTGTACGCTGTACGCTGAC 3' (SEQ ID NO:20)

The GTACGC type of element has been described as the U box by Plesse, et al., Mol. Gen. Gent. 254: 258-266 (1997). We have included two such elements in the promoter designed in this study only as an example. The number of copies that contribute to improved function may be variable.

We predict that the three types of domains i.e. a, b, c individually and their combinations in single or multiple copies can act in co-ordination with each other either in the sense or in the antisense direction. On the basis of our analysis the dataset developed by us, we predict that these can even be expected to work in other possible number of repeats, permutations and combinations. These domains were identified by us by theoretical analysis and used to design a promoter

```
5' GCTTGTACGC TGTACGCTGAC GATAGATAGATA CACGTGCACGCGT 3'   (SEQ ID No. 6)
        (c)           (b)            (a)
``` region targetting at high level expression of genes. Hence, the designed sequence is novel and does not resemble my natural promoter, as far as the sequence is concerned, and has no known example of a similar promoter reported in earlier studies.

The regions identified during our analysis mainly comprise of tandem repeats of 2-8 nt length, termed as domain II(a). They are mainly spread from the −130 to the −350 nt region. These repeats include purine rich elements, which have been identified for the first time in our analysis. These are $(A/G)_{2-8}$ (SEQ ID No. 7) or its complementary $(T/C)_{2-8}$ nt. As noticed in the dataset of highly expressing genes created by us, these elements are mainly present beyond −200 nt but may be present between −200 to −150 nt and less commonly before −130 nt. These may or may not have specific palindromic geometry. These types of elements may be separated by 2 to 200 nt from each other. The copy number of these elements may vary from 1-10 and less commonly may go up to 15.

Yet another sequence typical to the dataset of highly expressing genes and identified during this analysis is a C(A/T)(A/T)C(A/T)(A/T) (SEQ ID No. 8) type of element termed as domain II(b). These elements are generally present upstream of the promoter beyond −200 nt, but may less commonly be present between −200 to −150 nt and exceptionally may be located downstream of a gene. The location of these elements in the database suggests that these enhancer elements may act in the sense as well as in the antisense direction.

Another conserved element includes the SV40 type of enhancer, the role of these has been established in plant promoters, animal promoters and viral promoters. However, their usage in the form of an artificially designed promoter has not been discussed or reported. Use of several such elements in such a way that functional co-ordination is achieved in form of a synthesized promoter is a new concept. Furthermore, other variants of these sequences and those not reported earlier, like GGTAATAC (SEQ ID No. 9) termed as domain II(c) have been employed in designing the promoter. These elements are usually present after −200 nt upstream but less commonly occur before −130 nt.

Another 16 base pair palindromic sequence, 5' AC(G/A)(T/C)AAGCGCTTACGT 3' (SEQ ID NO:10), is the octopine enhancer type of element and it's variants, which may or may not be palindromic. These were identified during this study to be conserved in several highly expressed plant genes and termed as domain II(d). This element was located more usually around −200 bp upstream. It may be active in both sense and antisense directions. The activity of the natural ocs element was shown by Gelvin, et al. Proc. Natl. Acad. Sci. USA, 85: 2553-557 (1988). However its use in association with other elements to develop a synthetic promoter is a novel aspect of this invention.

DNA bending elements have been suggested to play an important role in bringing synergy between a basal promoter and the upstream activating region in animal cells. We have for the first time identified a potential DNA bending element in the highly expressed genes in plants i.e.

```
5' CGATCTGACCATCTCTAGATCG-3'    (SEQ ID No. 11)
```

This element is termed as domain III with respect to synthetic promoter. This site is surprisingly similar to the YY1 element identified in animal promoters as shown by Kim & Shipro, Nucl. Acids Res., 24: 4341-4348 (1996). The authors reported the potential of this element in anima cells to activate basal promoter. This elements is mostly present in between basal promoter and the upstream activator elements. This sequence is usually found upstream of −200. Identification of these elements in plants as well as the use of these elements in developing a synthetic promoter is a novel part of this invention.

The region between the transcription start site and the TATA box is also highly conserved and was identified by comparing several highly expressed genes. This region, viz.,

```
5' GGAAGTTCAT TTCATTTGGA ATGGA     (SEQ ID NO: 12)
CA3'
``` has not been identified earlier. It does not exactly resemble any known promoter and was computed purely by analysing the highly expressing genes and comparing the sequences with lowly expressed genes. Its length varies between 20-40 nucleotides but usually is around 26 bp. This DNA sequence may function by lowering the Tm, and hence is predicted to facilitate transcription bubble formation and increase transcription efficiency. To that extent, the use of this element as well as its variants with lower Tm (AT richness) is a part of the new principle employed by us in developing an artificial promoter.

The 5' untranslated leader region also modulates the level of expression, as per the scanning model proposed by Kozak Cell, 22: 7-8 (1980). The 40S subunit binds to the 5' cap end of eucaryotic mRNA. The efficiency of initiation of translation depends upon smooth scanning by a ribosome and efficient recognition of the AUG context to form a translational complex. Any strong hairpin formation in this region can adversely effect the ribosome scanning and reduce translational efficiency. We have analysed the sequences in the untranslated leader sequence (5' UL) of plant genes and discovered that the 5' UL of highly expressed genes more often varies from 75 to 90 nt while that of the lowly expressed genes showed relatively longer 5' UL ranging from 100-300 nt. and is sometimes intervened by an intron. We have identified 'CAA' type conserved sequences in the 5' untranslated leader region. The frequency of occurrence of CAA in highly expressed genes in a representative data employed by us was 3.6 elements, while that in the lowly expressed genes was 1.1 elements per 100 nucleotides of the leader sequence. The CAA sequences have been recognised as translational enhancers in TMV by Gallie and Waubot Nucl. Acids. Res, 20: 4361-4368 (1992), but their association with plant genes has not been reported earlier. The 5' UL used in this study is 81 nucleotides long. Care was taken to avoid 'G' in the 5' UL since our data suggest poor representation of 'G' in the 5' UL of highly expressed genes. According to the analysis, the artificial 5' UL was constructed for efficient scanning as per SEQ ID No 13.

We also compared the translation initiation codon AUG context (that determines the ribosome halting at AUG and initiation complex formation) among highly and lowly expressed genes. Improper context leads to bypassing of AUG by ribosomes, as shown by Kozak, J. Mol. Biol, 196: 947-950 (1987). We identified different contexts in different groups of plant genes which show significant differences in expression. The highly expressed genes show

AT(A/C)AACAATGGCTNCCNCNA (SEQ ID NO. 14)

in contrast to the lowly expressed genes in plants which show

GANATGGNGNNGNNANA (SEQ ID NO:15)

(Tables 4 & 5). SEQ ID NO:15 (although does not contain G after ATG). This indicated that the differences in the AUG context may be critical to achieve the desired level of gene expression. Analysis of the highly expressed genes, as seen in Table 4 suggests that the former sequence and its close variants allow high level expression of genes in nature. Hence, an artificial promoter targeted for high level of gene expression can have SEQ ID NO:14 or its variants to the extent given in Table 4.

A significant new finding emerges from the analysis of the first four codons in highly expressed genes in plants. As summarised in Table (6), the first four codons in highly expressed genes predominantly code for specific amino acids that may to stabilise proteins. The first triplet is always methionine, as known already. The second triplet predominantly codes for alanine, the third and fourth triplets code predominantly for serine. The predominant presence of methionine, alanine and serine at the N-terminus may confer stability to highly expressed proteins by enhancing their half life. This can facilitate their abundance. Our results suggested that following methionine and alanine at the first and the second positions, respectively, serine is the predominant amino acid at the third and often at the fourth position in highly expressed genes in plant cells. The use of DNA codons for these amino acids at the N-terminus in order to achieve high level expression of genes or high stability of the proteins is a novel finding of this invention.

The aforesaid information generated through the computational analysis was used to design a synthetic promoter targeted for high level expression of genes. The sequence of the promoter so designed doesn't resemble any of the natural promoters. The basis of the invention is to develop database with a subset of genes that express under a desired condition, identify the pool of cis-acting elements common to these genes and bring such elements together in a systematic way so as to achieve to desired level and pattern of transgene expression. The present study demonstrates the basis of promoter designing by targeting to develop a highly expressing constitutive promoter. The distances between the several cis elements can be variable within limits but do not match any known promoter. The sequence of an exemplary promoter is as per SEQ ID No1. Several natural promoters, like CaMV 35S promoter have been shown to function in unrelated organisms, like the yeast *Schizosacchromyces pombe* by Gmunder and Kohli, Mol. Gen. Genet, 220(1): 95-101 (1989) and animal tissue, like, *Xenopus* oocytes by Ballas et al., Nucl. Acids. Res 17(19):7891-7903. Several of the bacterial promoters have been reported to express in plant chloroplasts and vice versa, as in Brixey, et al. Biotechnology Letters 19:395-399 (1997) and Daniell, et al., Nature Biotechnology 16:345-348 (1998). The structural and functional conservation of several components of the transcriptional machinery in plants, animals and yeast i.e. in all eukaryotes has been reported by Gasch et al., Nature, 346:390-394 (1990) and Vogel et al., Plant Cell 5:1627-1638(1993). Therefore, the said artificial promoter designed and synthesised as described by us can be used to express foreign genes in plants, animals, bacteria and other lower organisms. Our prediction that such an artificial synthetic promoter will be expected to express in, several eukaryotes is therefore, logical. As shown by Odell et al., Nature 313:810-812 (1985), a strong promoter like the CaMV 35S promoter expresses in all parts of plants, like the stems, leaves, roots and flowers. The examples given herein demonstrate that the promoter designed by us as an example, for high level expression of genes, expresses efficiently in protoplasts; all parts of plants viz., leaves, stems and, roots; in different plant species, like tobacco, cabbage stem and potato tuber and also in bacterial cells.

As given in FIG. 1, the artificially designed promoter sequence was divided into 16 overlapping oligonucleotides, each of around ~50 nucleotides in length, for the purpose of synthesising the promoter chemically. Unique SalI and XbaI restriction enzyme sites were provided at 5' and 3' ends respectively to facilitate cloning. As seen in FIG. 2, other sites were also created inside the designed promoter sequence to facilitate future studies on various elements. The individual oligos were synthesised on a 'Pharmacia LKB Gene Assembler Secial'. These were purified using 10% denaturing PAGE and eluted in MilliQ water from polyacrylamide gel. Finally, the desalting was carried out using NAP 10 (Pharmacia) column. The assembly of the oligomers was carried out using the method described by Singh et al., J. Bioscience. 21 (6): 735-741 (1996). The assembled product was then cloned into the MCS of the SK+ bluescript plasmid vector (Stratagene).

All molecular biology protocols were followed as taught in Manual on Molecular Cloning (second edition) by Sambrook, Fritsch and Maniatis. The clones were sequenced using an Applied Biosystem DNA sequencer. The primer was designed for introduction of context in front of the uidA gene. The sequence of the primer is shown in FIG. (3). XbaI site was given at the end of primer. The downstream primer was designed from the MfeI site located about 150 bp in the uidA gene. The 150 bp fragment including the 5' end of uidA was then amplified using pBI 101.1 (Clonethch) as a template. The ~150 bp fragment so obtained for each different context was then excised from agarose gel and blunt end ligated to EcoRV cut SK+ bluescript plasmid. The clones were then sequenced using an automated sequencer as mentioned earlier.

The 2.3 kbp Mfe 1-Eco RI fragment of pBI 101 containing the uidA gene (downstram of MfeI site) with nos terminator was purified from agarose gel. This was ligated to the XbaI-MfeI ~150 bp fragment representing the context. The context-uidA constructs were cloned into PUC 19 cut with XbaI and EcoRI. Positive clones were selected on blue/white basis and confirmed by cuting with the internal sites. The SalI-XbaI fragment (434 bp) of the artificially designed synthetic promoter (ASP) so excised from the gel was ligated in front of each of these clones. Constructs with the synthetic promoter in front of uidA gene with context was named as pASP. Comparison was carried out between the synthetic and CaMV 35S promoters using biolistic and PEG mediated DNA delivery into leaf cells and protoplasts of tobacco, cabbage and potato tuber. Transient expression was measured on the basis of GUS expression using known techniques. The efficiency of synthetic promoter for expression in different parts of tobacco plant was also measured by developing stable transgenic plants of tobacco, following transformation by *Agrobacterium tumefaciens*.

The details of the process of the present invention are given below and illustrated with the help of examples but should not be construed to limit the scope of the invention:

EXAMPLE 1

Transient Expression of Synthetic Promoter by PEG Mediated Transformation of Tobacco Protoplasts.

Protoplasts were prepared by digesting fully expanded leaves of *Nicotiana tabacum* in enzyme mixture containing 0.625% Cellulase R 250 and 0.625% Macrozyme R 250 in K3A nutrient medium (Negritiu, et al., Plant Mol. Biol. 8: 363-373 (1987). Protoplasts were isolated by the floating method as per Negritiu et al ibid. $10^5$ protoplasts were sus pended into 0.3 ml PTN (Negritiu, et al., Plant Mol. Biol. 8: 363-373 (1987) solution. 50 μg of the DNA construct (carrying the artificial promoter with uidA gene) was then added immediately, followed by addition of 24% PEG (8000) to the final concentration of 10%. Equal volume of the K3A medium was added after 20 min of incubation. After 10 min, the total volume was made to 3.0 ml with K3A medium. The protoplasts were incubated at 28° C. for 24 h in the dark. After 24 h, protoplasts were pelleted down and washed with $W_5$ salt solution (Negritiu, et al., Plant Mol. Biol. 8: 363-373 (1987). Finally, protoplasts were suspended in GUS extraction buffer and lysed by sonication. Expression of GUS from uidA gene attached to the corresponding promoter was examined on the basis of hydrolysis of a fluorescent substrate called MUG i.e., 4-methyl umberiferryl gluconoride as described in Jefferson Plant. Mol. Biol. Reporter 5 (4): 387-405 (1987). The results of the expression are given in Table 7. The synthetic promoter expresses in tobacco protoplasts at levels three to four times higher than the native 35S CaMV promoter.

EXAMPLE 2

Comparison of 35S CaMV Promoter with Synthetic Promoter Using Biolistics Mediated Delivery in Tobacco Leaf.

The microprojectile mediated delivery of DNA containing the transgene (reporter gene i.e. uidA) driven by CaMV 35S or the synthetic promoter sequence (described in the present invention) was achieved in tobacco leaf, using a helium gas driven biolistics gun. The DNA was coated on gold particles of 1 μm size by mixing 3 mg particles (suspended in water) with 5 μg DNA constructs (suspension in 5 μl water), 50 μl calcium chloride (2.5 M stock solution) and 20 μl spermidine solution (0.1 M stock solution). The mixture was allowed to shake for 3 min and centrifuged briefly for 30 sec. The pellet was suspended well in 250 μl ethanol and centrifuged again briefly for 10 sec. The pellet was again resuspended in 60 μl ethanol. Such DNA coated particles were then bombarded on leaf discs of *Nicotiana tabacum* placed on MS agar medium, using a PDS 1000 He machine (Biorad Laboratory, USA). The plates were incubated under controlled light and temperature for a period of 48 h. The GUS assay was carried out as per Jefferson Plant Mol. Biol. Rep. (4): 387-405 (1987) The results given in Table 8 clearly demonstrate that the synthetic promoter causes expression of the uidA gene at a sixteen fold higher level in tobacco leaves as compared to the native 35S CaMV promoter.

EXAMPLE 3

Comparison of Transient Expression from CaMV 35S Promoter with that from Synthetic Promoter in Different Plant Species.

To examine the expression of the synthetic promoter in a variety of plant species and in different explants, the DNA was delivered by biolistics method as in Example 2. Cotton leaves, potato tubers and cabbage stem were selected for expression of the synthetic promoter vis a vis CaMV 35S promoter. Transient transformation was carried out using biolistics as described in example 2. Following the bombardment, the GUS assay was carried out using MUG substrate as per Jefferson, RA. Plant Mol. Biol. Rep. (4): 387-405 (1987). The results complied in Table 9, demonstrate that the synthetic promoter expressed at substantially higher level in different plant species and in a variety of explants. Thus the synthetic promoter designed by us expresses in a species and tissue independent manner at levels 2 to 20 times higher than the CaMV 35S promoter, following transient transformation.

EXAMPLE 4

Expression of the Designed Synthetic Promoter in Different Plant Parts in Stably Transformed Tobacco Plants.

A plant expression cassette was constructed by replacing SaI-EcoRI fragment of pBI 101.1 (Clontech) with the synthetic promoter-uidA-Nos cassette. The vector was inserted into a commonly used *Agrobacterium tumefaciens* strain LBA 4404 containing helper plasmid pAL4404, by electroporation. (Jun, S W and Forde, B G Nucl. Acids. Res. 17: 8385 (1987). Transgenic tobacco (*Nicotiana tabaccum* cv petit havana) were developed by cocultivation of tobacco leaf discs with *Agrobacterium tumefaciens* strain LBA 4404 (pAL 4404: pBIASP) for 48 hrs in dark. The cocultivation was performed on commonly used agar solidified MS (Murahsige and Skoog 1962) medium. Leaf discs were transferred to regeneration medium (MS medium+1.0 mg/L Benzyl amino purine+0.1 mg/L napthalene acetic acid) supplemented with 250 mg/L cefotaxime (to inhibit bacterial growth) and 100 mg/L kanamycin to select the transformed cells. The selection was performed for 4 weeks in 60 μmol $m^{-2}s^{-1}$ PAR (16 h photoperiod) and 24±2° C. in culture room. The shoots regenerated in the presence of kanamycin were excised and transferred to rooting medium (MS+0.1 mg/L naphthalene acetic acid+50 μg/L kanamycin). The shoots with well developed roots were obtained after 2-4 weeks culture under 60 μmol $m^{-3}s^{-1}$ PAR and 24±2° C. temperature. Two different transgenics in vitro regenerated plantlets at 4-6 leaf stage were sacrificed to check the activity of synthetic promoter in leaf, stem & root. The expression of uidA gene was checked by GUS assay using MUG as described by Jefferson, RA. Plant Mol. Biol. Rep. 4: 387-405 (1987). The results are compiled in Table 10. The syntheitc promoter shows a high level of activity in leaf, stem as well as root of Ro tobacco plants. However, quite noticeably, the activity in roots was at least five times higher in transgenic plantlets. Thus the synthetic promoter expresses at high level constitutively but has a preference for high expression in roots.

EXAMPLE 5

Expression of the Designed Synthetic Promoter in the Bacterium *Agrobacterium tumefaciens*.

To demonstrate that the synthetic promoter expressed in prokaryotes, the bacterium *Agrobacterium tumefaciens* was taken as an example. The construct pBIASP expressing uidA synthetic promoter and pBI121 (Clontech) from CaMV 35S promoter were transformed into *Agrobacterium* using electroporation as described by Jun, S W and Forde, B G Nucl. Acids Res 17: 8385 (1989). The freshly transformed cells were then grown overnight in LB medium supplemented with kanamycin (50 μg/ml) at 28° C. on shaker (250 rpm). The cells were then harvested using centrifugation at 12,000 rpm for 5 min. The cells were then suspended in GUS extraction buffer and lysed by sonication. Debris was then pelleted at 12,000 rpm for 10 min at 4° C. Supernatant was used for GUS assay as described by the Jefferson, R A Plant. Mol. Biol Rep 4: 387-405 (1987). The results in Table 10 demonstrate activity of the synthetic promoter in the bacterium. The synthetic promoter showed 10 fold higher activity as compared to the CaMV 35S promoter.

Although the foregoing invention has been described in some detail by way of illustrations and examples for the purposes of clarity of understanding, it is obvious that certain changes and modifications may be practised within the scope of the variation in context sequences noticed in the statistical analysis given in Tables 1 to 6 and appended in the claims.

```
INFORMATION FOR SEQ ID NO.:1
(I)    SEQUENCE CHARACTERISTICS:
       (A) LENGTH: 452 base pair
       (B) TYPE: DNA
       (C) STRANDEDNESS: SINGLE OR DOUBLE
       (D) TOPOLOGY: LINER OR CIRCULAR
(II)   MOLECULE TYPE: ARTIFICIAL
(III)  SEQUENCE DESCRIPTION: ARTIFICIAL SYNTHETIC PROMOTER -350
      ↓
  1 GTCGACCATCATTTGAAAGGGCCTCGGTAATACCATTGTGGAAAAAGTTG
                    DOMAIN II 51 GTAATACGGAAAAAGAAGATTCATCATCCAGAAAAGGTGTGGAAAAGTTG
                       -230              -209
                        ↓     DOMAIN III   ↓
101 TGGATTGCGTGGAAAAAGTTCGATCTGACCATCTCTAGATCGTGGAAAAA
            DOMAIN II 151 GTTCACGTAAGCGCTTACGTACATATGTGGATTGTGGAAAAAGAAGACGG
                    -130
                      ↓       DOMAIN I
201 AGGCATCGGTGGAAAAAGAAGCTTGTACGCTGTACGCTGACGATAGATAG -84
                 ↓    MINIMAL DOMAIN (b)
251 ATACACGTGCACGCGTCCACTTGACGCACAATTGACGCACAATGACGCCA
           -43  MINIMAL    -26
            ↓ DOMAIN (a)   ↓REGION BETWEEN TATA AND TS
301 CTTGACGCTACTTCACTATATATAGGAAGTTCATTTCATTTGGAATGGAC +1TS
      ↓
351 ACGTGTTGTCATTTCTCAACAATTACCAACAACAACAAACAACAAACAAC
          5' UNTRANSLATED LEADER          +89
                                            ↓
401 ATTATACAATTACTATTTACAATTACATCTAGATAAACAATGGCTTCCTCC
 +102
   ↓
450 A INFORMATION FOR SEQ ID NO:2
(I)    SEQUENCE CHARACTERISTICS:
       (A) LENGTH: 18 base pair
       (B) TYPE: DNA
       (C) STRANDEDNESS: SINGLE OR DOUBLE
       (D) TOPOLOGY: LINEAR OR CIRCULAR
(II)   MOLECULE TYPE: GENOMIC OR EXTRACHROMOSOMAL
(III)  SEQUENCE DESCRIPTION: TATA CONTEXT FOR HIGHLY EXPRESSED
       GENES

-43                    -26
5' (T/C)T(T/A)(T/C)NTCACTATATATAG3'

INFORMATION FOR SEQ ID NO:3
(I)    SEQUENCE CHARACTERISTICS:
       (A) LENGTH: 18 base pairs
       (B) TYPE: DNA
       (C) STRANDEDNESS: SINGLE OR DOUBLE
       (D) TOPOLOGY: LINEAR OR CIRCULAR
(II)   MOLECULE TYPE: GENOMIC OR EXTRACHROMOSOMAL
(III)  SEQUENCE DESCRIPTION: TATA CONTEXT FOR LOWLY EXPRESSED
       GENES

-43           -26
5' TTTNNNNTTTATANNNAT 3'

INFORMATION FOR SEQ ID NO:4
(I)    SEQUENCE CHARACTERISTICS:
       (A) LENGTH: 7 base pair
       (B) TYPE: DNA
       (C) STRANDEDNESS: SINGLE OR DOUBLE
       (D) TOPOLOGY: LINEAR OR CIRCULAR
(II)   MOLECULE TYPE: GENOMIC OR EXTRACHROMOSOMAL
```

(III) SEQUENCE DESCRIPTION: TRANSCRIPTION START SITE OF HIGHLY
    EXPRESSED GENES

```
    -6   +1
5' ANNNNCA 3'
```

INFORMATION FOR SEQ ID NO:5
(I)  SEQUENCE CHARACTERISTICS:
     (A) LENGTH: 46 base pair
     (B) TYPE: DNA
     (C) STRANDEDNESS: SINGLE OR DOUBLE
     (D) TOPOLOGY: LINEAR OR CIRCULAR
(II) MOLECULE TYPE: ARTIFICIAL, GENOMIC OR EXTRACHROMOSOMAL
(III)SEQUENCE DESCRIPTION: MINIMAL DOMAIN (b)

```
   -84
5'CCACTTGACGCACAATTGACGCACAATGACGCCACTTGACGCTACT3'
                                                -39
```

INFORMATION FOR SEQ ID NO:6
(I)  SEQUENCE CHARACTERISTICS:
     (A) LENGTH: 46 base pair
     (B) TYPE: DNA
     (C) STRANDEDNESS: SINGLE OR DOUBLE
     (D) TOPOLOGY: LINEAR OR CIRCULAR
(II) MOLECULE TYPE: ARTIFICIAL, GENOMIC OR EXTRACHROMOSOMAL
(III)SEQUENCE DESCRIPTION: DOMAIN I

```
  -130                                          -85
5'GCTTGTACGCTGTACGCTGACGATAGATAGATACACGTGCACGCGT3'
           c              b           a
```

INFORMATION FOR SEQ ID NO:7
(I)  SEQUENCE CHARACTERISTICS:
     (A) LENGTH: 8 base pair
     (B) TYPE: DNA
     (C) STRANDEDNESS: SINGLE OR DOUBLE
     (D) TOPOLOGY: LINEAR OR CIRCULAR
(II) MOLECULE TYPE: GENOMIC, EXTRACHROMOSOMAL OR ARTIFICIAL
(III)SEQUENCE DESCRIPTION: DOMAIN II(a)

```
5'(A/G)(A/G)(A/G)(A/G)(A/G)(A/G)(A/G)(A/G)3'
```

INFORMATION FOR SEQ ID NO:8
(I)  SEQUENCE CHARACTERISTICS:
     (A) LENGTH: 6 base pair
     (B) TYPE: DNA
     (C) STRANDEDNESS: SINGLE OR DOUBLE
     (D) TOPOLOGY: LINEAR OR CIRCULAR
(II) MOLECULE TYPE: GENOMIC OR EXTRACHROMOSOMAL
(III)SEQUENCE DESCRIPTION: DOMAIN II(b)

```
5'C(A/T)(A/T)C(A/T)(A/T)3'
```

INFORMATION FOR SEQ ID NO:9
(I)  SEQUENCE CHARACTERISTICS:
     (A) LENGTH: 8 base pair
     (B) TYPE: DNA
     (C) STRANDEDNESS: SINGLE OR DOUBLE
     (D) TOPOLOGY: LINEAR OR CIRCULAR
(II) MOLECULE TYPE: GENOMIC OR EXTRACHROMOSOMAL
(III)SEQUENCE DESCRIPTION: DOMAIN II(c)

```
5'GGTAATAC3'
```

INFORMATION FOR SEQ ID NO:10
(I)  SEQUENCE CHARACTERISTICS:
     (A) LENGTH: 16 base pair
     (B) TYPE: DNA
     (C) STRANDEDNESS: SINGLE OR DOUBLE
     (D) TOPOLOGY: LINEAR OR CIRCULAR
(II) MOLECULE TYPE: GENOMIC OR EXTRACHROMOSOMAL -continued (III) SEQUENCE DESCRIPTION: DOMAIN II(d)

5'AC(G/A)(C/T)AAGCGCTTACGT3'

INFORMATION FOR SEQ ID NO:11
(I)   SEQUENCE CHARACTERISTICS:
      (A) LENGTH: 22 base pair
      (B) TYPE: DNA
      (C) STRANDEDNESS: SINGLE OR DOUBLE
      (D) TOPOLOGY: LINEAR OR CIRCULAR
(II)  MOLECULE TYPE: GENOMIC OR EXTRACHROMOSOMAL
(III) SEQUENCE DESCRIPTION: DOMAIN III

-230                  -209
5'CGATCTGACCATCTCTAGATCG3'

INFORMATION FOR SEQ ID NO:12
(I)   SEQUENCE CHARACTERISTICS:
      (A) LENGTH: 27 base pair
      (B) TYPE: DNA
      (C) STRANDEDNESS: SINGLE OR DOUBLE
      (D) TOPOLOGY: LINEAR OR CIRCULAR
(II)  MOLECULE TYPE: ARTIFICIAL, GENOMIC OR EXTRACHROMOSOMAL
(III) SEQUENCE DESCRIPTION: REGION BETWEEN TATA BOX AND
      TRANSCRIPTION START

-26                      +1
5'GGAAGTTCATTTCATTTGGAATGGACA3'

INFORMATION FOR SEQ ID NO:13
(I)   SEQUENCE CHARACTERISTICS:
      (A) LENGTH: 89 base pair
      (B) TYPE: DNA
      (C) STRANDEDNESS: SINGLE OR DOUBLE
      (D) TOPOLOGY: LINEAR OR CIRCULAR
(II)  MOLECULE TYPE: ARTIFICIAL, GENOMIC OR EXTRACHROMOSOMAL
(III) SEQUENCE DESCRIPTION: 5' UNTRANSLATED LEADER +1
5'ACGTGTTGTCATTTCTCAACAATTACCAACAACAACAA
ACAACAACAACATTATACAATTACTATTTACAATTACA
TCTAGATAAACA3'
            +89

INFORMATION FOR SEQ ID NO:14
(I)   SEQUENCE CHARACTERISTICS:
      (A) LENGTH: 30 base pair
      (B) TYPE: DNA
      (C) STRANDEDNESS: SINGLE OR DOUBLE
      (D) TOPOLOGY: LINEAR OR CIRCULAR
(II)  MOLECULE TYPE: GENOMIC OR EXTRACHROMOSOMAL
(III) SEQUENCE DESCRIPTION: ATG CONTEXT FOR HIGHLY EXPRESSED
      GENES

+83                +102
5'AT(A/C)AACAATGGCTNCCNCNA3'

INFORMATION FOR SEQ ID NO:15
(I)   SEQUENCE CHARACTERISTICS:
      (A) LENGTH: 18 base pair
      (B) TYPE: DNA
      (C) STRANDEDNESS: SINGLE OR DOUBLE
      (D) TOPOLOGY: LINEAR OR CIRCULAR
(II)  MOLECULE TYPE: GENOMIC OR EXTRACHROMOSOMAL
(III) SEQUENCE DESCRIPTION: ATG CONTEXT FOR LOWLYLY EXPRESSED
      GENES

+87         +103
5'GANATGGNGNNGNNANA3'

INFORMATION FOR SEQ ID NO:16
(I)   SEQUENCE CHARACTERISTICS:
      (A) LENGTH: 4 amino acid
      (B) TYPE: PROTEIN

```
    (C) STRANDEDNESS: NA
    (D) TOPOLOGY: LINEAR
(II) MOLECULE TYPE: CELLULAR
(III)SEQUENCE DESCRIPTION: N-TERMINAL AMINO ACIDS FOR HIGHLY
    EXPRESSED PROTEIN

AA1          AA4
N-MET-ALA-SER-SER-C
```

TABLE 1

Analysis of sequences around TATA region of highly expressed genes in plants

| Position | −44 | −43 | −42 | −41 | −40 | −39 | −38 | −37 | −36 | −35 | −34 | −33 | −32 | −31 | −30 | −29 | −28 | −27 | −26 |
|---|---|---|---|---|---|---|---|---|---|---|---|---|---|---|---|---|---|---|---|
| A (%) | 27 | 21 | 20 | 36 | 20 | 30 | 2 | 1 | 57 | 10 | 0 | 97 | 1 | 99 | 27 | 99 | 15 | 93 | 6 |
| T (%) | 36 | 39 | 40 | 38 | 34 | 25 | 68 | 20 | 18 | 17 | 100 | 0 | 98 | 1 | 73 | 1 | 85 | 3 | 15 |
| G (%) | 13 | 10 | 8 | 5 | 17 | 17 | 4 | 12 | 20 | 3 | 0 | 0 | 0 | 0 | 0 | 0 | 0 | 3 | 59 |
| C (%) | 24 | 30 | 32 | 21 | 29 | 28 | 26 | 67 | 5 | 70 | 0 | 3 | 1 | 0 | 0 | 0 | 0 | 1 | 20 |
| * | N | N | N | N | N | N | T | C | A | C | T | A | T | A | T | A | T | A | G |
| ** | T | T | T | T/A | T | N | T | C | A | C | T | A | T | A | T | A | T | A | G |

\* Consensus as per Cavener, Nucleic Acids res. 15: 1353-1361 (1987)
\*\* Consensus as per $\chi^2$ test (at P ≥ 0.05% occurrence to be ≥34)

TABLE 2

Analysis of sequences around TATA region of lowly expressed genes in plants

| Position | −43 | −42 | −41 | −40 | −39 | −38 | −37 | −36 | −35 | −34 | −33 | −32 | −31 | −30 | −29 | −28 | −27 | −26 |
|---|---|---|---|---|---|---|---|---|---|---|---|---|---|---|---|---|---|---|
| A (%) | 0 | 7 | 7 | 0 | 14 | 7 | 21 | 14 | 14 | 0 | 100 | 7 | 100 | 50 | 42 | 56 | 77 | 7 |
| T (%) | 85 | 64 | 64 | 50 | 42 | 57 | 28 | 70 | 63 | 100 | 0 | 84 | 0 | 50 | 35 | 28 | 0 | 70 |
| G (%) | 0 | 14 | 7 | 14 | 14 | 7 | 14 | 7 | 0 | 0 | 0 | 0 | 0 | 0 | 21 | 16 | 14 | 21 |
| C (%) | 15 | 15 | 22 | 36 | 30 | 29 | 37 | 9 | 23 | 0 | 0 | 9 | 0 | 0 | 2 | 0 | 9 | 2 |
| * | T | T | T | T/C | N | T/C | N | T | T | T | A | T | A | A/T | A/T | A | A | T |
| ** | T | T | T | N | N | N | N | T | T | T | A | T | A | N | N | N | A | T |

\* Consensus as per Cavener
\*\* Consensus as per $\chi^2$ test (at P ≥ 0.05% occurrence to be ≥61)

TABLE 3

Analysis of sequences around transcription start site in highly expressed genes in plants

| Position | −10 | −9 | −8 | −7 | −6 | −5 | −4 | −3 | −2 | −1 | +1 |
|---|---|---|---|---|---|---|---|---|---|---|---|
| A (%) | 23 | 21 | 27 | 22 | 40 | 30 | 26 | 32 | 34 | 23 | 62 |
| T (%) | 35 | 35 | 35 | 35 | 27 | 26 | 31 | 37 | 28 | 25 | 28 |
| G (%) | 16 | 25 | 11 | 15 | 11 | 10 | 10 | 6 | 11 | 12 | 4 |
| C (%) | 26 | 19 | 27 | 28 | 22 | 34 | 33 | 25 | 27 | 40 | 6 |
| * | N | N | N | N | N | N | N | N | N | N | A |
| ** | N | N | N | N | A | N | N | N | N | C | A |

\* Consensus as per Cavener
\*\* Consensus as per $\chi^2$ test (at P ≥ 0.05% occurrence to be ≥36)

TABLE 4

Analysis of sequences around initiation codon of highly expressed genes in plants

| Position | +74 | +75 | +76 | +77 | +78 | +79 | +80 | +81 | +82 | +83 | +84 | +85 | +86 | +87 | +88 | +89 |
|---|---|---|---|---|---|---|---|---|---|---|---|---|---|---|---|---|
| A (%) | 32 | 43 | 37 | 32 | 37 | 38 | 32 | 31 | 36 | 40 | 22 | 45 | 88 | 80 | 18 | 92 |
| T (%) | 25 | 18 | 19 | 19 | 19 | 22 | 25 | 30 | 32 | 29 | 61 | 10 | 4 | 6 | 3 | 1 |
| G (%) | 14 | 11 | 16 | 17 | 25 | 16 | 17 | 17 | 11 | 12 | 8 | 5 | 3 | 10 | 0 | 0 |
| C (%) | 29 | 28 | 28 | 32 | 19 | 24 | 26 | 22 | 21 | 19 | 9 | 40 | 5 | 4 | 79 | 7 |
| * | N | N | N | N | N | N | N | N | N | T | A/C | A | A | C | A |
| ** | N | A | A | N | A | A | N | A | A | T | A/C | A | A | C | A |

TABLE 4-continued

Analysis of sequences around initiation codon of highly expressed genes in plants

| Position | +90 | +91 | +92 | +93 | +94 | +95 | +96 | +97 | +98 | +99 | +100 | +101 | +102 | +103 | +104 |
|---|---|---|---|---|---|---|---|---|---|---|---|---|---|---|---|
| A (%) | 100 | 0 | 0 | 0 | 2 | 10 | 25 | 15 | 20 | 34 | 24 | 22 | 40 | 22 | 34 |
| T (%) | 0 | 100 | 0 | 2 | 0 | 76 | 31 | 20 | 23 | 34 | 21 | 34 | 16 | 34 | 19 |
| G (%) | 0 | 0 | 100 | 98 | 4 | 12 | 26 | 7 | 15 | 17 | 10 | 19 | 25 | 9 | 15 |
| C (%) | 0 | 0 | 0 | 0 | 94 | 2 | 18 | 58 | 42 | 15 | 45 | 25 | 19 | 35 | 32 |
| * | A | T | G | G | C | T | N | C | N | N | N | N | N | N | N |
| ** | A | T | G | G | C | T | N | C | C | N | C | N | A | N | N |

* Consensus as per Cavener
** Consensus as per $\chi^2$ test (at P ≧ 0.05% occurrence to be ≧35)

TABLE 5

Analysis of sequences around initiation codon of lowly expressed genes in plants

| Position | +74 | +75 | +76 | +77 | +78 | +79 | +80 | +81 | +82 | +83 | +84 | +85 | +86 | +87 | +88 | +89 |
|---|---|---|---|---|---|---|---|---|---|---|---|---|---|---|---|---|
| A (%) | 39 | 25 | 32 | 30 | 31 | 27 | 32 | 25 | 31 | 31 | 30 | 20 | 37 | 38 | 57 | 36 |
| T (%) | 15 | 21 | 16 | 24 | 12 | 21 | 29 | 27 | 14 | 16 | 14 | 25 | 20 | 11 | 14 | 7 |
| G (%) | 11 | 23 | 19 | 16 | 27 | 32 | 11 | 28 | 19 | 25 | 29 | 26 | 28 | 41 | 8 | 38 |
| C (%) | 35 | 31 | 33 | 30 | 30 | 20 | 28 | 20 | 36 | 28 | 27 | 29 | 15 | 10 | 21 | 19 |
| * | N | N | N | N | N | N | N | N | N | N | N | N | N | G/A | A | N |
| ** | N | N | N | N | N | N | N | N | N | N | N | N | N | G | A | N |

| Position | +90 | +91 | +92 | +93 | +94 | +95 | +96 | +97 | +98 | +99 | +100 | +101 | +102 | +103 | +104 |
|---|---|---|---|---|---|---|---|---|---|---|---|---|---|---|---|
| A (%) | 100 | 0 | 0 | 21 | 33 | 11 | 32 | 33 | 20 | 24 | 17 | 41 | 29 | 44 | 20 |
| T (%) | 0 | 100 | 0 | 5 | 14 | 23 | 20 | 28 | 19 | 20 | 24 | 17 | 10 | 17 | 28 |
| G (%) | 0 | 0 | 100 | 67 | 21 | 42 | 28 | 29 | 48 | 40 | 27 | 23 | 37 | 16 | 32 |
| C (%) | 0 | 0 | 0 | 7 | 32 | 24 | 20 | 10 | 13 | 16 | 32 | 19 | 24 | 23 | 20 |
| * | A | T | G | G | N | N | N | N | N | N | N | N | N | N | N |
| ** | A | T | G | G | N | G | N | N | G | N | N | A | N | A | N |

* Consensus as per Cavener
** Consensus as per $\chi^2$ test (at P ≧ 0.05% occurrence to be ≧40)

TABLE 6

Percentage occurrence of amino acids at the first five positions coded by the highly expressed plant genes

| Amino Acid | AA 1 | AA 2 | AA 3 | AA 4 |
|---|---|---|---|---|
| Lysine | 0 | 0 | 4 | 13 |
| Aspargine | 0 | 0 | 2 | 7 |
| Serine | 0 | 1 | 28 | 30 |
| Glutamic acid | 0 | 0 | 4 | 3 |
| Isoleucine | 0 | 0 | 2 | 4 |
| Argenine | 0 | 0 | 2 | 4 |
| Threonine | 0 | 0 | 10 | 6 |
| Alanine | 0 | 97 | 13 | 7 |
| Aspartic acid | 0 | 0 | 7 | 2 |
| Glycine | 0 | 1 | 2 | 2 |
| Valine | 0 | 1 | 3 | 4 |
| Glutamine | 0 | 0 | 1 | 4 |
| Histidine | 0 | 0 | 1 | 2 |
| Tyrosine | 0 | 0 | 3 | 0 |
| Proline | 0 | 0 | 1 | 0 |
| Leucine | 0 | 0 | 13 | 7 |
| Phenyl alanine | 0 | 0 | 0 | 3 |
| Cystine | 0 | 0 | 2 | 1 |
| Methionine | 100 | 0 | 2 | 1 |

TABLE 7

Functional comparison of CaMV 35S promoter with that of artificial synthetic promoter using PEG mediated tobacco protoplast expression system

| PROMOTER | MUG ASSAY (pmole/h/mg protein) |
|---|---|
| ARTIFICIAL | 2000 |
| 35S | 550 |

TABLE 8

Functional comparison of CaMV 35S promoter with that of artificial synthetic promoter using biolistic mediated DNA delivery in leaf tissue of tobacco

| PROMOTER | NUMBER OF BLUE SPOTS | SIZE OF BLUE SPOTS | MUG ASSAY (pmole/h/mg protein) |
|---|---|---|---|
| ARTIFICIAL | +++++++ | ++++ | 7380 |
| 35S | ++ | ++ | 443 |

TABLE 9

Comparison of transient expression from CaMV 35S promoter with that from the designed synthetic promoter in different plant species.

| | Activity pmole of MU/h/mg protein | |
|---|---|---|
| Plants | CaMV 35S promoter | Artificial synthetic promoter |
| 1) Tobacco (leaves) | 443 | 7380 |
| 2) Cotton (leaves) | 376 | 5640 |
| 3) Potato (tuber) | 2867 | 4166 |
| 4) Cabbage (stem) | 3657 | 3983 |

TABLE 10

Expression of the designed synthetic promoter in different plant parts in stably transformed tobacco plants.

| | Activity pmole of MU/h/mg protein | |
|---|---|---|
| Plant Part | Transgenic line 1 | Transgenic line 2 |
| Leaf | 29400 | 35300 |
| Stem | 35362 | 27750 |
| Root | 104412 | 136537 |

TABLE 11

Expression of the designed synthetic promoter in the bacterium *Agrobacterium tumefaciens*
Activity pmole of MU/h/mg protein

| CaMV 35S promoter | Artificial synthetic promoter |
|---|---|
| $2.3 \times 10^4$ | $26 \times 10^4$ |

SEQUENCE LISTING

```
<160> NUMBER OF SEQ ID NOS: 20

<210> SEQ ID NO 1
<211> LENGTH: 452
<212> TYPE: DNA
<213> ORGANISM: Artificial
<220> FEATURE:
<223> OTHER INFORMATION: synthetic DNA promoter sequence

<400> SEQUENCE: 1
gtcgaccatc atttgaaagg gcctcggtaa taccattgtg gaaaaagttg gtaatacgga      60
aaaagaagat tcatcatcca gaaaaggtgt ggaaaagttg tggattgcgt ggaaaaagtt     120
cgatctgacc atctctagat cgtggaaaaa gttcacgtaa gcgcttacgt acatatgtgg     180
attgtggaaa aagaagacgg aggcatcggt ggaaaaagaa gcttgtacgc tgtacgctga     240
cgatagatag atacacgtgc acgcgtccac ttgacgcaca attgacgcac aatgacgcca     300
cttgacgcta cttcactata tataggaagt tcatttcatt tggaatggac acgtgttgtc     360
atttctcaac aattaccaac aacaacaaac aacaaacaac attatacaat tactatttac     420
aattacatct agataaacaa tggcttcctc ca                                   452

<210> SEQ ID NO 2
<211> LENGTH: 18
<212> TYPE: DNA
<213> ORGANISM: Artificial
<220> FEATURE:
<223> OTHER INFORMATION: TATA context for highly expressed genes
<220> FEATURE:
<221> NAME/KEY: misc_feature
<223> OTHER INFORMATION: "n" may be a, c, g, or t

<400> SEQUENCE: 2
ytwyntcact atatatag                                                    18

<210> SEQ ID NO 3
<211> LENGTH: 18
<212> TYPE: DNA
<213> ORGANISM: Artificial
<220> FEATURE:
<223> OTHER INFORMATION: TATA context for lowly expressed genes
<220> FEATURE:
```

```
<221> NAME/KEY: misc_feature
<223> OTHER INFORMATION: "n" may be a, c, g, or t

<400> SEQUENCE: 3
tttnnnnttt atannnat                                                 18

<210> SEQ ID NO 4
<211> LENGTH: 7
<212> TYPE: DNA
<213> ORGANISM: Artificial
<220> FEATURE:
<223> OTHER INFORMATION: transcription start site context
<220> FEATURE:
<221> NAME/KEY: misc_feature
<223> OTHER INFORMATION: "n" may be a, c, g, or t

<400> SEQUENCE: 4 annnnca                                                              7

<210> SEQ ID NO 5
<211> LENGTH: 46
<212> TYPE: DNA
<213> ORGANISM: Artificial
<220> FEATURE:
<223> OTHER INFORMATION: minimal domain (b)

<400> SEQUENCE: 5
ccacttgacg cacaattgac gcacaatgac gccacttgac gctact                  46

<210> SEQ ID NO 6
<211> LENGTH: 46
<212> TYPE: DNA
<213> ORGANISM: Artificial
<220> FEATURE:
<223> OTHER INFORMATION: domain I

<400> SEQUENCE: 6
gcttgtacgc tgtacgctga cgatagatag atacacgtgc acgcgt                  46

<210> SEQ ID NO 7
<211> LENGTH: 8
<212> TYPE: DNA
<213> ORGANISM: Artificial
<220> FEATURE:
<223> OTHER INFORMATION: domain II(a)

<400> SEQUENCE: 7 rrrrrrrr                                                             8

<210> SEQ ID NO 8
<211> LENGTH: 6
<212> TYPE: DNA
<213> ORGANISM: Artificial
<220> FEATURE:
<223> OTHER INFORMATION: domain II(b)

<400> SEQUENCE: 8 cwwcww                                                               6

<210> SEQ ID NO 9
<211> LENGTH: 8
<212> TYPE: DNA
<213> ORGANISM: Artificial
<220> FEATURE:
<223> OTHER INFORMATION: domain II(c)

<400> SEQUENCE: 9
```

-continued

```
ggtaatac                                                           8

<210> SEQ ID NO 10
<211> LENGTH: 16
<212> TYPE: DNA
<213> ORGANISM: Artificial
<220> FEATURE:
<223> OTHER INFORMATION: domain II(d)

<400> SEQUENCE: 10
acryaagcgc ttacgt                                                 16

<210> SEQ ID NO 11
<211> LENGTH: 22
<212> TYPE: DNA
<213> ORGANISM: Artificial
<220> FEATURE:
<223> OTHER INFORMATION: domain III

<400> SEQUENCE: 11
cgatctgacc atctctagat cg                                          22

<210> SEQ ID NO 12
<211> LENGTH: 27
<212> TYPE: DNA
<213> ORGANISM: Artificial
<220> FEATURE:
<223> OTHER INFORMATION: region between minimal promoter (a) and
      transcription start site

<400> SEQUENCE: 12
ggaagttcat ttcatttgga atggaca                                     27

<210> SEQ ID NO 13
<211> LENGTH: 89
<212> TYPE: DNA
<213> ORGANISM: Artificial
<220> FEATURE:
<223> OTHER INFORMATION: 5' untranslated leader region

<400> SEQUENCE: 13
acgtgttgtc atttctcaac aattaccaac aacaacaaac aacaaacaac attatacaat 60
tactatttac aattacatct agataaaca                                   89

<210> SEQ ID NO 14
<211> LENGTH: 20
<212> TYPE: DNA
<213> ORGANISM: Artificial
<220> FEATURE:
<223> OTHER INFORMATION: translational initiation codon context for
      highly expressed genes
<220> FEATURE:
<221> NAME/KEY: misc_feature
<223> OTHER INFORMATION: "n" may be a, c, g, or t

<400> SEQUENCE: 14
atmaacaatg gctnccncna                                             20

<210> SEQ ID NO 15
<211> LENGTH: 17
<212> TYPE: DNA
<213> ORGANISM: Artificial
<220> FEATURE:
<223> OTHER INFORMATION: translational initiation codon context for
      lowly expressed genes
<220> FEATURE:
```

```
<221> NAME/KEY: misc_feature
<223> OTHER INFORMATION: "n" may be a, c, g, or t

<400> SEQUENCE: 15
ganatggngn ngnnana                                                17

<210> SEQ ID NO 16
<211> LENGTH: 4
<212> TYPE: PRT
<213> ORGANISM: Artificial
<220> FEATURE:
<223> OTHER INFORMATION: N-terminal amino acids

<400> SEQUENCE: 16

Met Ala Ser Ser
1

<210> SEQ ID NO 17
<211> LENGTH: 58
<212> TYPE: DNA
<213> ORGANISM: Artificial
<220> FEATURE:
<223> OTHER INFORMATION: primer for introduction of ATG context into
      synthetic DNA promoter sequence

<400> SEQUENCE: 17
aattacatct agataaacaa tggcttcctc cgtagaaacc ccaacccgtg aaatcaaa      58

<210> SEQ ID NO 18
<211> LENGTH: 13
<212> TYPE: DNA
<213> ORGANISM: Artificial
<220> FEATURE:
<223> OTHER INFORMATION: domain I(a)

<400> SEQUENCE: 18
cacgtgcacg cgt                                                    13

<210> SEQ ID NO 19
<211> LENGTH: 12
<212> TYPE: DNA
<213> ORGANISM: Artificial
<220> FEATURE:
<223> OTHER INFORMATION: domain I(b)

<400> SEQUENCE: 19
gatagataga ta                                                     12

<210> SEQ ID NO 20
<211> LENGTH: 21
<212> TYPE: DNA
<213> ORGANISM: Artificial
<220> FEATURE:
<223> OTHER INFORMATION: domain I(c)

<400> SEQUENCE: 20
gcttgtacgc tgtacgctga c                                           21
```

We claim:

1. A promoter comprising at least one of each of the following elements, or functional fragments thereof, in the 5' to 3' direction: (i) domain II which comprises subdomain II(a), wherein subdomain II(a) is SEQ ID NO: 7;

(ii) domain I, which comprises subdomain I(a), wherein subdomain I (a) is SEQ ID NO: 18, or subdomain I(a) is a functional sequence with at least 75% sequence identity to SEQ ID NO: 18;

(iii) minimal domain (b), wherein minimal domain (b) is SEQ ID NO: 5;

(iv) minimal domain (a), wherein minimal domain (a) is SEQ ID NO: 2;

(v) region between minimal promoter (a) and a transcription start site context, wherein said region between minimal promoter (a) and said transcription start site context is SEQ ID NO: 12;

(vi) transcription start site context, wherein said transcription start site context is SEQ ID NO: 4;

(vii) 5' untranslated leader region, wherein said 5' untranslated leader region is SEQ ID NO: 13;

(viii) translational initiation codon context, wherein said translational initiation codon context is SEQ ID NO: 14; and (ix) a polynucleotide encoding the amino acid sequence set forth in SEQ ID NO. 16.

2. A method for testing the level of expression of a polynucleotide, comprising:

a) transforming a plant protoplast with a test construct, wherein said test construct comprises a polynucleotide encoding a target or reporter polypeptide operably linked with the 3' end of the promoter of claim 1 and wherein said polynucleotide is in frame with the polynucleotide encoding SEQ ID NO: 16 of said promoter, b) performing a transient GUS assay using the transformed plant protoplast of (a), and c) comparing the assay results of (b) with results from a transient GUS assay performed using a plant protoplast transformed with a control construct, wherein said control construct comprises said polynucleotide encoding a target or reporter polypeptide of (a) operably linked with a CaMV 35 S promoter, thereby testing the level of expression of a polynucleotide.

3. The method of claim 2, wherein said plant protoplast is a protoplast selected from the group consisting of a tobacco protoplast, a cotton protoplast, a cabbage protoplast and a potato protoplast.

4. The method of claim 2, wherein the protoplast is derived from a plant tissue.

5. The method of claim 4, wherein the plant tissue is a plant tissue selected from the group consisting of a root, shoot, leaf and storage tissue.

6. The method of claim 2, wherein the polynucleotide encoding a target or reporter polypeptide is uidA.

7. The method of claim 2, wherein said transformation is performed using polyethylene glycol-mediated transformation or biolistic-mediated transformation.

* * * * *